US011457820B2

United States Patent
Pikkula et al.

(10) Patent No.: US 11,457,820 B2
(45) Date of Patent: *Oct. 4, 2022

(54) ORAL EXAMINATION

(71) Applicant: Forward Science Technologies, LLC, Stafford, TX (US)

(72) Inventors: Brian Pikkula, Sugar Land, TX (US); Robert Whitman, Houston, TX (US)

(73) Assignee: Forward Science Technologies, LLC, Stafford, TX (US)

( * ) Notice: Subject to any disclaimer, the term of this patent is extended or adjusted under 35 U.S.C. 154(b) by 512 days.

This patent is subject to a terminal disclaimer.

(21) Appl. No.: 16/560,911

(22) Filed: Sep. 4, 2019

(65) Prior Publication Data

US 2019/0387976 A1 Dec. 26, 2019

Related U.S. Application Data

(63) Continuation of application No. 14/654,302, filed as application No. PCT/US2013/048159 on Jun. 27, (Continued)

(51) Int. Cl.
*A61B 5/00* (2006.01)
*A61B 1/06* (2006.01)
(Continued)

(52) U.S. Cl.
CPC .......... *A61B 5/0088* (2013.01); *A61B 1/0646* (2013.01); *A61B 1/0684* (2013.01);
(Continued)

(58) Field of Classification Search
CPC ....... A61B 1/06; A61B 1/0646; A61B 1/0684; A61B 1/24; A61B 1/247; A61B 5/0088; A61B 5/4552; A61C 1/088
See application file for complete search history.

(56) References Cited

U.S. PATENT DOCUMENTS 3,020,396 A 2/1962 Worboys
4,527,223 A 7/1985 Maglica
(Continued)

FOREIGN PATENT DOCUMENTS

EP 1693021 A1 8/2005
WO WO 2009-097154 A1 8/2009
WO WO 2014-123567 A1 8/2014

OTHER PUBLICATIONS

U.S. Appl. No. 14/654,302, filed Jun. 19, 2015.
(Continued)

*Primary Examiner* — Larry E Waggle, Jr.
(74) *Attorney, Agent, or Firm* — Leydig, Voit & Mayer, Ltd.

(57) ABSTRACT

A housing containing an electrical energy source is coupled between a first end cap comprising a control and an interstitial member comprising an LED selectively electrically couplable to the electrical energy source by the control, and a second end cap coupled to the interstitial member comprises an optical filtering component in optical alignment with light emitted by the LED. At least a portion of an exterior of at least one of the housing, the first end cap, the interstitial member, and the second end cap may have a cross-sectional shape that is not substantially circular. The end caps, housing, interstitial member, and optical filtering component may each be sealingly interconnected. A method of using the apparatus may comprise directing light emitted by the apparatus into a human oral cavity without inserting the apparatus into the human oral cavity.

16 Claims, 4 Drawing Sheets

Related U.S. Application Data 2013, now Pat. No. 10,413,191, which is a continuation-in-part of application No. 29/445,273, filed on Feb. 8, 2013, now Pat. No. Des. 715,937.

(51) Int. Cl.
*A61B 1/24* (2006.01)
*A61C 1/08* (2006.01)

(52) U.S. Cl.
CPC .............. *A61B 1/24* (2013.01); *A61B 5/4552* (2013.01); *A61C 1/088* (2013.01)

(56) References Cited

U.S. PATENT DOCUMENTS

| | | | |
|---|---|---|---|
| 4,757,381 A * | 7/1988 | Cooper | H04N 5/2256 433/116 |
| 5,586,819 A | 12/1996 | Bamber | |
| 6,176,596 B1 | 1/2001 | Shukla | |
| 6,231,207 B1 | 5/2001 | Kennedy | |
| 6,588,917 B1 | 7/2003 | Halasz | |
| 7,004,600 B2 | 2/2006 | Echterling | |
| 7,802,898 B1 | 9/2010 | Gregory et al. | |
| 8,337,201 B1 | 12/2012 | Mace | |
| 8,469,526 B1 | 6/2013 | Chung | |
| 8,750,969 B2 | 6/2014 | DiNardo et al. | |
| 8,786,689 B1 * | 7/2014 | Liu | A61B 1/24 348/68 |
| D715,937 S | 10/2014 | Pikkula et al. | |
| 9,217,558 B2 | 12/2015 | Sparing | |
| 10,413,191 B2 * | 9/2019 | Pikkula | A61B 1/24 |
| 2003/0021109 A1 | 1/2003 | Matthews | |
| 2003/0137834 A1 | 7/2003 | Jigamian | |
| 2003/0189826 A1 | 10/2003 | Yoon | |
| 2004/0012955 A1 | 1/2004 | Hsieh | |
| 2004/0190286 A1 | 9/2004 | Chapman | |
| 2004/0190299 A1 | 9/2004 | Chapman | |
| 2005/0073849 A1 | 4/2005 | Rhoads | |
| 2005/0080343 A1 | 4/2005 | Richards-Kortum et al. | |
| 2005/0085690 A1 * | 4/2005 | Tien | A61B 1/042 348/E7.087 |
| 2005/0099805 A1 | 5/2005 | Chapman | |
| 2005/0122714 A1 | 6/2005 | Matthews | |
| 2005/0168976 A1 | 8/2005 | Chen | |
| 2005/0168979 A1 | 8/2005 | Chen | |
| 2005/0174782 A1 | 8/2005 | Chapman | |
| 2006/0028809 A1 | 2/2006 | Huang | |
| 2006/0110701 A1 * | 5/2006 | Cwik | A61B 1/0669 433/29 |
| 2006/0256563 A1 | 11/2006 | Uke | |
| 2008/0062505 A1 | 3/2008 | Ouyang | |
| 2008/0253114 A1 | 10/2008 | Wen | |
| 2008/0272714 A1 | 11/2008 | Noble | |
| 2009/0091925 A1 | 4/2009 | Hesse | |
| 2009/0323344 A1 | 12/2009 | Crawford et al. | |
| 2010/0033961 A1 | 2/2010 | Palmer | |
| 2010/0033963 A1 | 2/2010 | Maglica | |
| 2010/0040993 A1 * | 2/2010 | Karazivan | A61L 2/07 433/29 |
| 2010/0234762 A1 * | 9/2010 | Pond | A61K 49/0056 433/29 |
| 2010/0254149 A1 | 10/2010 | Gill | |
| 2010/0315805 A1 | 12/2010 | Dongpan | |
| 2011/0063824 A1 | 3/2011 | Qiu | |
| 2011/0085324 A1 | 4/2011 | Liu | |
| 2011/0134632 A1 | 6/2011 | Hu | |
| 2011/0164411 A1 | 7/2011 | Sparing | |
| 2013/0183633 A1 * | 7/2013 | Dillon | A61B 1/00048 433/29 |

OTHER PUBLICATIONS

Moro et al., *ACTA Otorhinolaryngologica Italica*, 35: 449-454 (2015).
Dinardo et al., *Societa Italiana di Igiene ,48 Congresso Nazionale* (2015).
Abati et al., *XIII Congresso Nationale Societa Italiana di Patologia e Medicina Orale* (2015).
Moro et al., *J Craniofacial Surgery*, 21: 1899-1903 (2010).

* cited by examiner

ORAL EXAMINATION

CROSS-REFERENCE TO RELATED APPLICATIONS

The present application is a continuation of copending U.S. patent application Ser. No. 14/654,302, filed on Jun. 19, 2015, which is the U.S. National Phase of International Patent Application No. PCT/US2013/048159, entitled "Oral Examination," filed Jun. 27, 2013, which claims the benefit of and priority to U.S. Design Pat. Application No. 29/445,273, entitled "Oral Cancer Screening Device," filed Feb. 8, 2013, which issued as D715,937 on Oct. 21, 2014, the entire disclosures of which are hereby incorporated herein by reference.

BACKGROUND OF THE DISCLOSURE

In oral cancer screening, abnormal tissue can be distinguished from healthy tissue using different tests and/or techniques. These may include using dyes, biopsies, or cancer screening lights. Current tests require the use of a disposable and/or otherwise have high costs associated with more frequent use.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
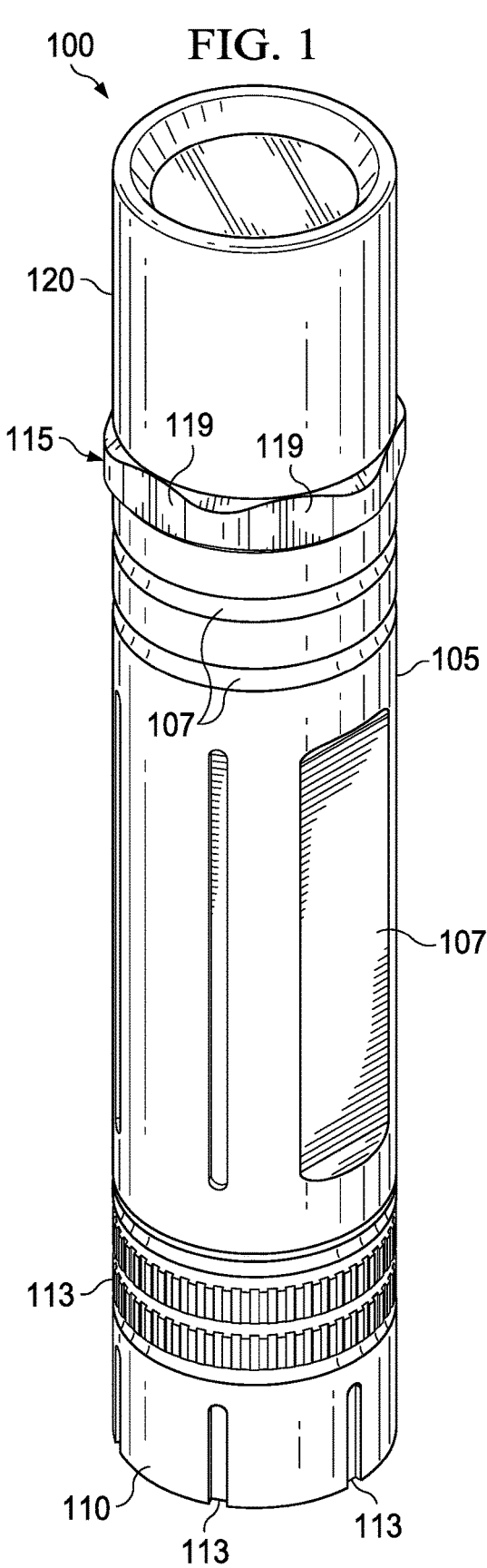
FIG. 1 is a schematic view of at least a portion of apparatus according to one or more aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 2:
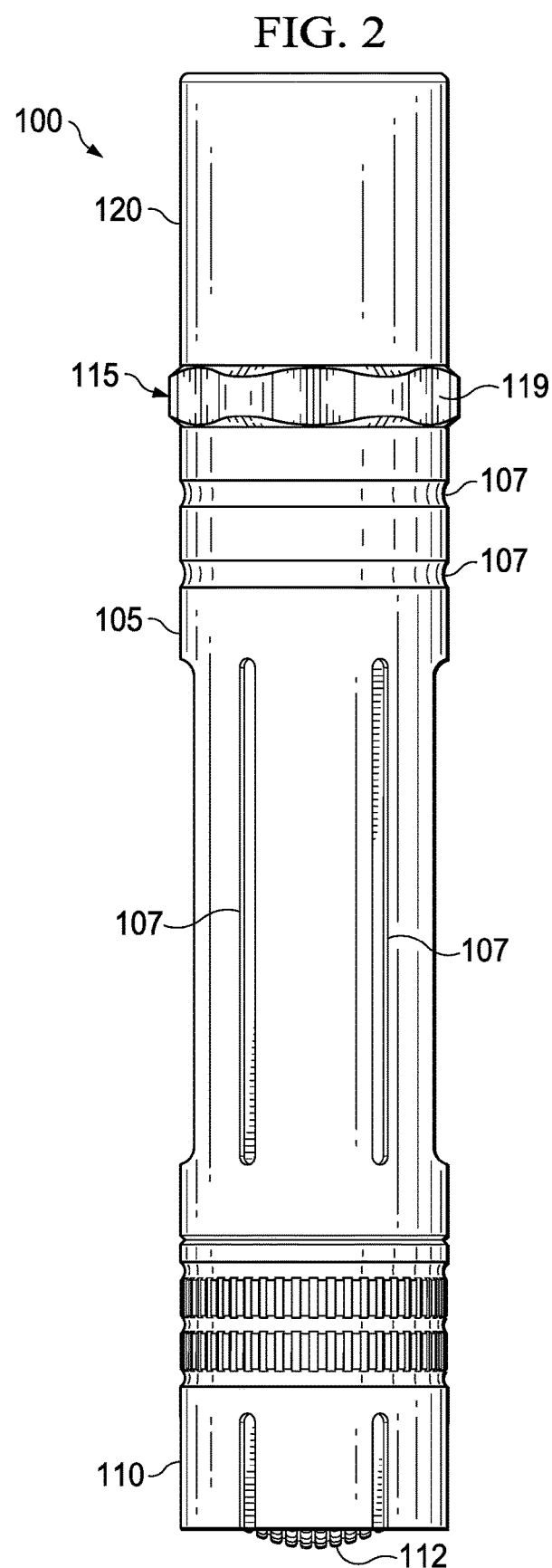
FIG. 2 is a schematic view of at least a portion of apparatus according to one or more aspects of the present disclosure.
Figure 3:
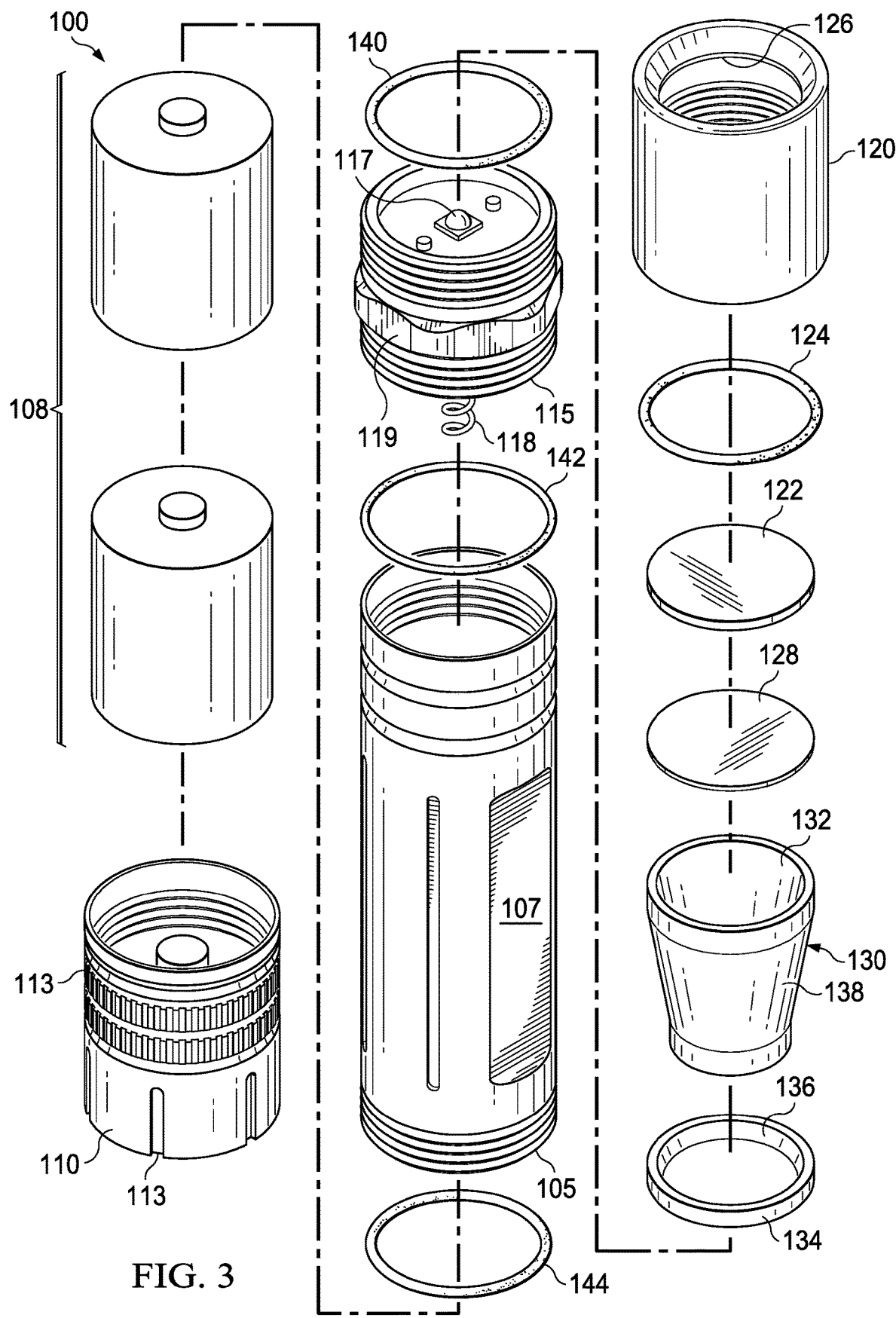
FIG. 3 is a schematic view of at least a portion of apparatus according to one or more aspects of the present disclosure.

FIGS. 1-3 are perspective, front, and exploded views, respectively, of at least a portion of apparatus 100 according to one or more aspects of the present disclosure. Referring to FIGS. 1-3 collectively, the apparatus 100 may comprise a housing 105, a first end cap 110, an interstitial member 115, and a second end cap 120, all coupled end-to-end in the order listed, as shown in FIG. 1. However, the housing 105, the first end cap 110, the interstitial member 115, and the second end cap 120, a subset thereof, and/or additional components may be coupled or otherwise interconnected in a manner other than as shown in FIG. 1, and such implementations are also within the scope of the present disclosure.

The housing 105 may be or comprise a partially or substantially cylindrical tube. One or more recessed and/or protruding features 107 may be formed integrally with or otherwise coupled to the housing 105. Such features may extend axially along at least a portion of the housing 105, circumferentially around at least a portion of the housing 105, or a combination thereof, which may assist with securely gripping the apparatus 100. Opposing ends of the housing 105 may be threaded and/or otherwise configured to couple with the first end cap 110 and the interstitial member 115. For example, in the implementation depicted in FIGS. 1 and 2, the housing 105 comprises external threads to couple with the first end cap 110 and internal threads to couple with the interstitial member 115. Of course, other means for coupling the first end cap 110 and/or the interstitial member 115 with the housing 105 are also within the scope of the present disclosure. The housing 105 may comprise metal, plastic, and/or other substantially rigid materials, perhaps including materials that may be disinfected and/or sterilized by conventional and/or future-developed processes, such as for use in a dental office and/or other medical environments.

The housing 105 contains an electrical energy source 108, which in the implementation depicted in FIG. 3 comprises two batteries. The batteries may be alkaline, NiCd, NiMH, NiZn, lithium, lithium ion, silver-oxide, galvanic, electrolytic, wet cells, dry cells, and/or other types of batteries. For example, the batteries may be CR123A batteries, such as those available from ENERGIZER and DURACELL. In other implementations, the electrical energy source 108 may comprise components other than batteries, such as circuitry for connection to a facility electrical system, or a mechanically powered energy source that generates electrical power by shaking, squeezing, winding, and/or otherwise moving the housing 105 and/or another component of the apparatus 100.

The first end cap 110 may comprise a control 112 (FIG. 2) operable to electrically connect the electrical energy source 108 to other electronic components of the apparatus 100 described below. For example, the control 112 may comprise a push button control, a rotatable knob, and/or a switch, although other control types are also within the scope of the present disclosure. The first end cap 110 may also comprise one or more patterned, recessed, and/or protruding portions 113, such as may assist in removing and/or assembling the first end cap 110 to the housing 105.

The interstitial member 115 comprises a light source 117 that may be selectively energized by the electrical energy source 108 via operation of the control 112. The light source 117 may comprise one or more light emitting diodes (LEDs). For example, the light source 117 may be an LED that emits in the blue and/or violet sections of the visible spectrum, such as at a wavelength of about 450 nm or otherwise in the range of about 350 nm to about 500 nm. Intensity of the light energy emitted by the light source 117 may be about 500 mW or otherwise in the range of about 75 mW to about 2000 mW. However, other means may also or alternatively be utilized for the light source 117 within the scope of the present disclosure.

The interstitial member 115 may also comprise one or more components forming an electrical path between the electrical energy source 108 and the light source 117. For example, such an electrical path may comprise a spring and/or other member 118 extending from the interstitial member 115 to the electrical energy source 108, and/or various electronic components and/or circuitry, perhaps including one or more LED drivers, resistors, capacitors, transformers, voltage cut-off coils, low-pass filters, high-pass filters, integrated circuits, and/or others (not shown).

The second end cap 120 comprises an optical filtering component 122 that is in substantial optical alignment with the light source 117 and/or light emitted therefrom. The optical filtering component 122 may be or comprise a low-pass filter and/or a high-pass filter, although other filters are also within the scope of the present disclosure. An O-ring 124 may be positioned between the optical filtering component 122 and an inside lip 126 of the second end cap 120, such as to create a seal prevent fluid from entering the apparatus via the interface between the optical filtering component 122 and the inside lip 126. The second end cap 120 may further comprise a diffuser 128 positioned to diffuse the light emitted by the light source 117 before the light is incident upon the optical filter component 122, such as to reduce the sharpness of the edges of the beam of light emitted by the light source 117. The optical filtering component 122 and/or the diffuser 128 may comprise glass, plastic, and/or other materials providing the appropriate optical characteristics.

A reflector 130 may also be positioned at least partially within the second end cap 120 in substantial optical alignment between the light source 117 and the optical filtering component 122. An internal surface 132 of the reflector 130 may be polished, painted, and/or otherwise configured to centrally focus the light energy emitted by the light source 117. The reflector 130 may comprise metal, plastic, and/or any other suitable material, and may be secured within the second end cap 120 by a retaining ring 134. For example, the retaining ring 134 may have an internal sloped surface 136 configured to cooperate with an external sloped surface 138 of the reflector 130, such that threading and/or otherwise assembling the retaining ring 134 into corresponding internal threads and/or other features of the second end cap 120 urges the sloped surfaces 136 and 138 together, thus urging the reflector 130 towards the internal lip 126 of the second end cap 120 and compressing the O-ring 124 to form the desired seal. The cooperating sloped surfaces 136 and 138 may also center the reflector 130 relative to a longitudinal axis of the second end cap 120 and/or otherwise aid in optically aligning the reflector 130 between the light source 117 and the optical filtering component 122.

At least a portion of an exterior of at least one of the housing 105, the first end cap 110, the interstitial member 115, and the second end cap 120 may have a cross-sectional shape that is not substantially circular. For example, as shown in the implementation depicted in FIGS. 1-3, a portion of the external surface of the interstitial member 115 may comprise one or more flats 119, such as may aid in preventing the apparatus 100 from rolling when resting on a substantially horizontal surface. However, one or more of the housing 105, the first end cap 110, and the second end cap 120 may alternatively or additionally comprise one or more such features. In addition to the flats 119 shown in FIGS. 1-3, or as an alternative thereto, the cross-sectional shape of the housing 105, the first end cap 110, the interstitial member 115, and/or the second end cap 120 may have at least a portion that is square, rectangular, elliptical, and/or otherwise substantially non-circular. Such features may be integrally formed with one or more corresponding components of the apparatus 100, and/or may be discrete members that are coupled to one or more of such components.

At least a portion of an exterior surface of one or more of the housing 105, the first end cap 110, the interstitial member 115, and the second end cap 120 may also comprise a material that provides substantial gripping force, such as rubber and/or other pliable materials. Such gripping features may be the same as the anti-roll features described above.

As described above, the interface between the optical filtering component 122 and the internal lip 126 of the second end cap 120 may be sealed and/or otherwise made waterproof by compression of the interposing O-ring 124. The interconnection of the other components of the apparatus 100 may also comprise similar sealing and/or other features. For example, the interface between the second end cap 120 and the interstitial member 115 may be sealed and/or otherwise made waterproof by compression of a similar O-ring 140 and/or other means. Similarly, the interface between the interstitial member 115 and the housing 105 may be sealed and/or otherwise made waterproof by compression of a similar O-ring 142 and/or other means. The interface between the housing 105 and the first end cap 110 may also be sealed and/or otherwise made waterproof by compression of a similar O-ring 144 and/or other means. The O-rings 124, 140, 142, and 144 and/or additional or alternative sealing means may seal and/or otherwise make the apparatus 100 waterproof such that, once the apparatus 100 is assembled, no fluids may enter any internal cavity of the apparatus 100.

Having described various details and alternatives with respect to the apparatus 100 shown in FIGS. 1-3, operation of the apparatus 100 will now be described with reference to FIG. 4, which is a schematic view of a dentist, hygienist, and/or other medical personnel 410 utilizing the apparatus 100 to perform oral examination of a patient 420, such as to identify oral cancer, pre-cancer, and/or other oral mucosal abnormalities. The apparatus 100 may be made commercially available as part of a kit that also contains one or more eyewear devices 430 to be worn by the medical personnel 410 and, perhaps, the patient 420 during the oral examination procedure.

The eyewear devices 430 may comprise an optical filtering component to be utilized in conjunction with the optical filtering component 122 shown in FIGS. 1-3. For example, the lenses of the eyewear device(s) 430 may comprise a low-pass filter, and the optical filtering component 122 of the apparatus 100 may comprise a high-pass filter. Alternatively, the lenses of the eyewear device(s) 430 may comprise a high-pass filter, and the optical filtering component of the apparatus 100 may comprise a low-pass filter. In either case, the combination of the filters is operable in conjunction with the light emitted by the apparatus 100 to detect cancerous and/or pre-cancerous regions and/or other mucosal abnormalities of the oral cavity of the patient 420. That is, the two filters may remove all (or substantially all) light emitted by the apparatus 100, including that which may reflect off of surfaces of the oral cavity of the patient 420, such that only the light resulting from fluorescence of the mucosal abnormalities remains visible to the medical personnel 410. Alternatively, the two filters and the light emitted by the apparatus 100 may work in conjunction to dim any light other than the fluorescence emanating from the mucosal abnormalities. The patient 420 may also wear an eyewear device 430 to, for example, block at least a portion of the light emitted by the apparatus 100 from entering their eyes.

Figure 4:
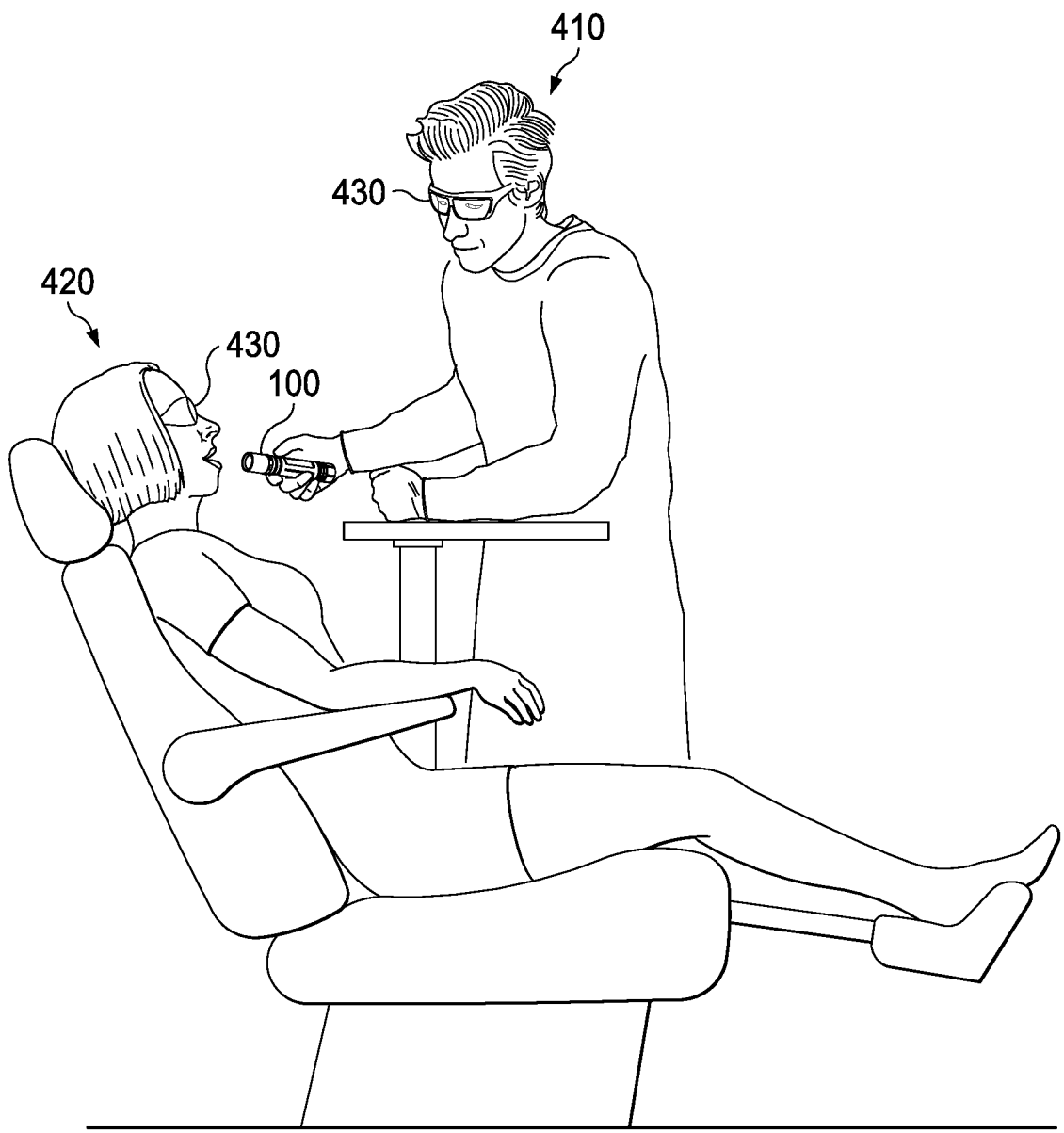
FIG. 4 is a schematic view of at least a portion of apparatus according to one or more aspects of the present disclosure.
Figure 5:
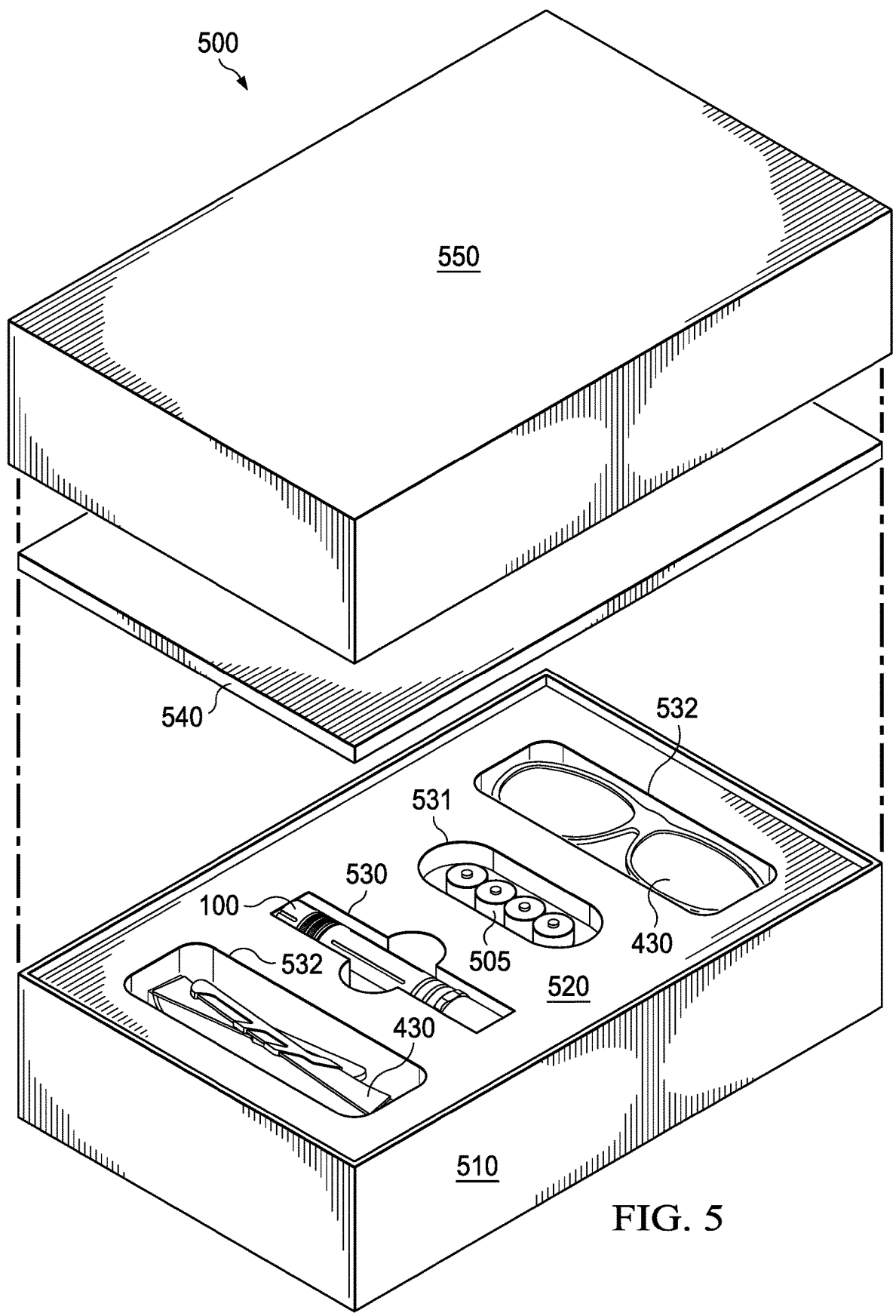
FIG. 5 is a schematic view of at least a portion of a kit according to one or more aspects of the present disclosure.

FIG. 5 is a schematic view of a kit 500 according to one or more aspects of the present disclosure. The kit 500 may comprise one or more instances of the apparatus 100 shown in FIGS. 1-4 and one or more of the eyewear devices 430 shown in FIG. 4. In the example implementation depicted in FIG. 5, the kit 500 also comprises spare batteries and/or other components 505 of the electrical energy source 108 shown in FIG. 2. The components of the kit 500 may be packaged in one or more boxes and/or other containers 510, perhaps within an insert 520 having recessed features 530-532 sized to receive corresponding components of the kit 500, such as may aid in protecting the components of the kit from mechanical shocks and/or other forces that may be experienced during handling, shipping, and/or otherwise. For example, the insert 520 may comprise foam and/or other shock-absorbing materials, and may have a first feature 530 sized to receive the apparatus 100 in a manner substantially preventing movement of the apparatus 100 within the container 510. Similarly, a second feature 531 may be sized to receive a predetermined number of batteries (four being shown in FIG. 5), and third features 532 may each be sized to receive one of the eyewear devices 430. Each of the second and third features 531 and 532 may also substantially prevent movement of the batteries and eyewear devices within the container 510. The kit 500 may also comprise an additional insert 540 covering the components of the kit 500 before a cover 550 is assembled to the container 510.

Figure 6:
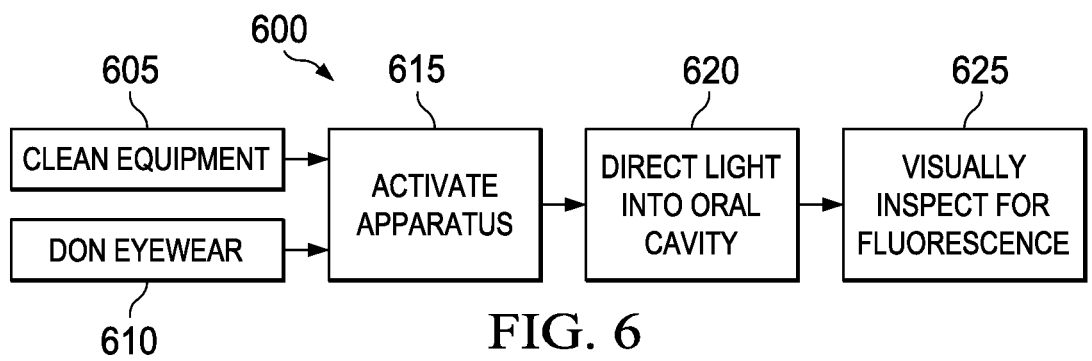
FIG. 6 is a flow-chart diagram of at least a portion of a method according to one or more aspects of the present disclosure.

FIG. 6 is a flow-chart diagram of at least a portion of a method 600 according to one or more aspects of the present disclosure. The method 600 may utilize at least a portion of the apparatus described above, such as the apparatus 100 shown in FIGS. 1-5 and/or the eyewear devices 430 shown in FIGS. 4 and 5.

The method 600 may comprise cleaning (605) one or more pieces of equipment to be utilized during the method 600. For example, this may entail cleaning the apparatus 100 shown in FIGS. 1-5 and/or the eyewear devices 430 shown in FIGS. 4 and 5. Such cleaning may comprise disinfecting and/or sterilizing the equipment. For example, the apparatus 100 shown in FIGS. 1-5 and/or the eyewear devices 430 shown in FIGS. 4 and 5 may be submersed in a sanitizing solution, such as CAVICIDE (available from UNIMED), MAXICIDE (available from HENRY SCHEIN, INC., and isopropyl alcohol, although other disinfecting and/or sanitizing products may also or alternatively be utilized. Disinfecting and/or sterilizing the equipment may also or alternatively comprise autoclaving and/or thoroughly wiping the equipment with a sanitizing fabric, paper, and/or other wipe.

The method 600 may also comprise donning (610) an eyewear device, such as the eyewear device 430 shown in FIGS. 4 and 5. This may entail one or both of the medical personnel and the patient donning the eyewear.

The light-emitting apparatus 100 shown in FIGS. 1-5 may then be activated (615). As described above, such activation may be via operation of a control of the apparatus, such as a push-button, rotating knob, switch, and/or other control. After activating the apparatus, the medical personnel may then direct (620) light emitted by the activated apparatus into the oral cavity of the patient. For example, the medical personnel may position the light emitting apparatus proximate the patient's oral cavity and orient the apparatus such that all or a substantial portion of the emitted light enters the patient's oral cavity. However, this procedure does not include inserting the light-emitting apparatus into the patient's oral cavity. Thereafter, the medical personnel may visually inspect (625) for fluorescence emitted by cancerous areas, pre-cancerous areas, and/or other mucosal abnormalities of the patient's oral cavity by looking through the eyewear.

The order of the above-described portions of the method 600 may vary within the scope of the present disclosure. For example, the equipment cleaning may be performed prior to activating the light-emitting apparatus and/or after directing the emitted light into the patient's oral cavity. It is also noteworthy that the method 600 does not include utilizing any type of disposable that is discarded after each iteration of the method. For example, the method 600 does not include assembling a rigid or flexible plastic sleeve over the light-emitting apparatus, and thus does not include disposing of such sleeves.

In view of the entirety of the present disclosure, including FIGS. 1-6, a person having ordinary skill in the art should readily recognize that the present disclosure introduces an apparatus comprising: a housing; a member coupled to the housing and comprising a light emitting diode (LED); and one or more end caps coupled to the housing and collectively comprising: a control operable to selectively electrically couple the LED to an electrical energy source; and an optical filtering component in optical alignment with light emitted by the LED; wherein at least a portion of an exterior of at least one of the housing, the member, and the one or more end caps has a cross-sectional shape that is not substantially circular. The electrical energy source may be completely contained within the housing. The electrical energy source may comprise a battery. The electrical energy source may comprise a rechargeable battery.

At least a portion of the exterior of the housing may have the cross-sectional shape that is not substantially circular. At least a portion of the exterior of the member may have the cross-sectional shape that is not substantially circular. The housing may be substantially cylindrical. The control may comprise a push-button control, a rotatable knob, and/or a switch.

The LED may be operable to emit light in the violet and/or blue wavelength spectrum.

The optical filtering component may comprise at least one of a low-pass filter and a high-pass filter.

The member may be an interstitial member coupled to a first end of the housing, and the one or more end caps may comprise: a first end cap coupled to a second end of the housing and comprising the control; and a second end cap coupled to the interstitial member opposite the housing and comprising the optical filtering component. The second end cap may comprise a reflector optically aligned between the LED and the optical filtering component and operable to focus the light emitted by the LED before the light is incident on the optical filtering component. The apparatus may further comprise a retaining ring threadedly coupled to an interior surface of the second end cap and extending around an external circumference of the reflector. The retaining ring may have a beveled inner perimeter, and the reflector may have a beveled outer perimeter operable to slidingly engage the beveled inter perimeter of the retaining ring, thereby centering the reflector within the second end cap.

At least a portion of the exterior of at least one of the housing, the member, and the one or more end caps may have one or more substantially flat portions and/or a gripping material.

The present disclosure also introduces an apparatus comprising: a housing; an electrical energy source contained within the housing; a first end cap sealingly coupled to a first end of the housing and comprising a control; an interstitial member sealingly coupled to a second end of the housing, wherein the interstitial member comprises a light emitting diode (LED), and wherein the control is operable to selectively electrically couple the electrical energy source to the LED; and a second end cap sealingly coupled to the interstitial member opposite the housing and comprising an optical filtering component in optical alignment with light emitted by the LED, wherein the optical filtering component is sealingly coupled to an end of the second end cap opposite the interstitial member.

The housing may be substantially cylindrical.

At least a portion of the exterior of at least one of the housing, the first end cap, the interstitial member, and the second end cap may have one or more substantially flat portions and/or a gripping material.

The apparatus may further comprise a sealing member coupled between the first end cap and the first end of the housing, a sealing member coupled between the interstitial member and the second end of the housing, a sealing member coupled between the second end cap and the interstitial member, and/or a sealing member coupled between the optical filtering component and the end of the second end cap.

The electrical energy source may comprise a battery, including a rechargeable battery.

The control may comprise a push-button control, a rotatable knob, and/or a switch.

The LED may be operable to emit light in the violet and/or blue wavelength spectrum.

The optical filtering component may comprise at least one of a low-pass filter and a high-pass filter.

The second end cap may comprise a reflector optically aligned between the LED and the optical filtering component and operable to focus the light emitted by the LED before the light is incident on the optical filtering component. The apparatus may further comprise a retaining ring threadedly coupled to an interior surface of the second end cap and extending around an external circumference of the reflector. The retaining ring may have a beveled inner perimeter, and the reflector may have a beveled outer perimeter operable to slidingly engage the beveled inter perimeter of the retaining ring, thereby centering the reflector within the second end cap.

The present disclosure also introduces a method comprising: activating an oral examination device that comprises: a housing; a member coupled to the housing and comprising a light emitting diode (LED); and one or more end caps collectively comprising: a control operable to selectively activate the oral examination device by electrically coupling the LED to an electrical energy source; and an optical filtering component in optical alignment with light emitted by the LED; and directing light emitted by the activated oral examination device into a human oral cavity by orienting the oral examination device relative to the human oral cavity without inserting the oral examination device into the human oral cavity.

The electrical energy source may be completely contained within the housing. The electrical energy source may comprise a battery. The electrical energy source may comprise a rechargeable battery.

The member may be an interstitial member, and the one or more end caps may comprise: a first end cap coupled to a first end of the housing and comprising the control; and a second end cap coupled to the interstitial member opposite the housing and comprising the optical filtering component in optical alignment with light emitted by the LED.

The method may exclude using a disposable.

The method may further comprise disinfecting and/or sterilizing the oral examination device.

The method may further comprise disinfecting the oral examination device by submersing the oral examination device in a sanitizing liquid.

The method may further comprise sterilizing the oral examination device by autoclaving the oral examination device.

The method may further comprise disinfecting the oral examination device by wiping the oral examination device with a sanitizing wipe.

The method may further comprise donning eyewear associated with the oral examination device. Donning the eyewear may be performed by a medical personnel and the human. The eyewear may comprise an optical filtering component. The optical filtering component may comprise at least one of a low-pass filter and a high-pass filter.

The control may comprise a push-button control, and activating the oral examination device may comprise operating the push-button control.

The present disclosure also introduces a kit comprising: an oral examination device comprising: a housing; a member coupled to the housing and comprising a light emitting diode (LED); and one or more end caps collectively comprising: a control operable to selectively electrically couple the LED to an electrical energy source; and an optical filtering component in optical alignment with light emitted by the LED; and eyewear associated with the oral examination device and comprising an optical filtering component.

The housing may completely receive the electrical energy source therein.

The kit may further comprise a plurality of spare batteries to be positioned within the oral examination device.

The kit may further comprise a container containing an insert, and the insert may comprise a plurality of recesses each receiving one of the oral examination device and the eyewear.

At least a portion of an exterior of at least one of the housing, the member, and the one or more end caps may have a cross-sectional shape that is not substantially circular.

The member may be an interstitial member, and the one or more end caps may comprise: a first end cap coupled to the housing and comprising the control; and a second end cap coupled to the interstitial member and comprising the optical filtering component. The first end cap may be sealingly coupled to a first end of the housing. The interstitial member may be sealingly coupled to a second end of the housing. The second end cap may be sealingly coupled to the interstitial member. The optical filtering component may be sealingly coupled to the second end cap.

The kit may not include a disposable discarded after each use of the oral examination device.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to allow the reader to quickly ascertain the nature of the technical disclosure. It is submitted with the understanding that it will not be used to interpret or limit the scope or meaning of the claims.

What is claimed is:

1. An oral cavity (pre-)cancer and/or mucosal abnormality screening apparatus comprising:
   a light emitting device comprising a first optical filtering component optically aligned to a light emitting diode (LED), and a reflector optically aligned between the LED and the first optical filtering component,
   wherein the reflector is operable to focus light emitted by the LED before the light is incident on the first optical filtering component and the LED is operable to emit light in the violet or blue wavelength spectrum at an intensity from about 75 mW to about 2000 mW, and
   an eyewear device comprising a second optical filtering component,
   wherein the first optical filtering component comprises a low-pass filter or a high-pass filter, which is configured to be in optical communication with the second optical filtering component on the eyewear device, the second optical filtering component comprising a high-pass filter corresponding to the low-pass filter of the first optical filtering component or a low pass filter corresponding to the high-pass filter of the first optical filtering component, wherein the low-pass filter and high-pass filter have overlapping cutoff frequencies to enable visual observation of the (pre-)cancer and/or mucosal abnormalities in an oral cavity.

2. The apparatus of claim 1, wherein the first and second optical filtering components are collectively configured to filter substantially all the light emitted by the LED, including that which reflects off of surfaces of the oral cavity.

3. The apparatus of claim 1, wherein the first optical filtering component comprises the low-pass filter and the second optical filtering component comprises the high-pass filter.

4. The apparatus of claim 1, wherein the first optical filtering component comprises the high-pass filter and the second optical filtering component comprises the low-pass filter.

5. The apparatus of claim 1, wherein the LED emits light at a wavelength in the range of about 350 nm to about 500 nm.

6. The apparatus of claim 5, wherein the LED emits light at a wavelength of about 450 nm.

7. The apparatus of claim 1, wherein the LED emits light at an intensity of about 500 mW.

8. A method of observing (pre-)cancer and/or mucosal abnormalities in a human oral cavity comprising:
   activating the light emitting device of claim 1 such that the light emitting device emits light,
   donning the eyewear device of claim 1, and
   directing the light emitted by the light emitting device into a human oral cavity by orienting the light emitting device relative to the human oral cavity without inserting light emitting device into the human oral cavity.

9. The method of claim 8, further comprising sterilizing the light emitting device, disinfecting the light emitting device, or a combination thereof.

10. The method of claim 9, wherein the light emitting device is sterilized by autoclaving the light emitting device.

11. The method of claim 9, wherein the light emitting device is disinfected by submersing the light emitting device in a sanitizing liquid.

12. The method of claim 9, wherein the light emitting device is disinfected by wiping the light emitting device with a sanitizing wipe.

13. A kit comprising the light emitting device of claim 1 and the eyewear device of claim 1.

14. The kit of claim 13, further comprising a container having an insert that comprises at least two recesses for the light emitting device and the eyewear device.

15. The kit of claim 13, further comprising spare batteries.

16. The kit of claim 15, further comprising a container having an insert that comprises at least three recesses for the light emitting device, the eyewear device, and the spare batteries.

* * * * *